United States Patent [19]

Ehrenkranz

[11] 4,408,905
[45] Oct. 11, 1983

[54] URINARY TEMPERATURE MEASUREMENT DEVICE

[76] Inventor: Joel R. L. Ehrenkranz, 12 Crest Cir., South Orange, N.J. 07079

[21] Appl. No.: 272,689

[22] Filed: Jun. 11, 1981

[51] Int. Cl.³ .......................................... G01K 11/12
[52] U.S. Cl. .................... 374/157; 374/141; 374/162; 4/144.1; 4/144.2; 128/736; 128/738; 128/761
[58] Field of Search ............... 374/162, 161, 157, 141; 4/144.1, 144.2; 128/736, 738, 760, 761; 436/65

[56] References Cited

U.S. PATENT DOCUMENTS

| | | | |
|---|---|---|---|
| 2,204,764 | 6/1940 | Mayo | 374/171 |
| 2,927,463 | 3/1960 | Stubbs | 128/738 X |
| 3,625,654 | 12/1971 | Duyne | 128/760 X |
| 3,651,695 | 3/1972 | Brown | 374/147 |
| 3,696,675 | 10/1972 | Gilmour | 374/162 X |
| 3,864,976 | 2/1975 | Parker | 374/161 |
| 3,871,230 | 3/1975 | Dye et al. | 73/215 |
| 4,151,831 | 5/1979 | Lester | 128/736 |

FOREIGN PATENT DOCUMENTS 2155020 10/1973 Fed. Rep. of Germany ...... 128/760

OTHER PUBLICATIONS

Fox et al., "Measurement of Deep Body Temperature from the Urine", *Clinical Science and Molecular Medicine*, 48(1975), pp. 1-7.
Murray et al., "Urinary Temperature", *New England Journal of Medicine*, v. 296, No. 1, 1977, pp. 23-24.

*Primary Examiner*—Herbert Goldstein
*Assistant Examiner*—J. Chapman
*Attorney, Agent, or Firm*—LeBlanc, Nolan, Shur & Nies

[57] ABSTRACT

A device for accurately measuring core body temperature by measuring urine temperature is disclosed. The device consists of a sampling chamber including an insulated liquid crystal temperature array which will instantaneously display the temperature of the urine sample therein. The device of this invention is useful as an accurate measurement of the fertility cycles in females, and for the detection of ovulation and pregnancy. The device is also useful in the detection of hypoglycemia, hypothermia and fever.

7 Claims, 6 Drawing Figures

U.S. Patent        Oct. 11, 1983        4,408,905
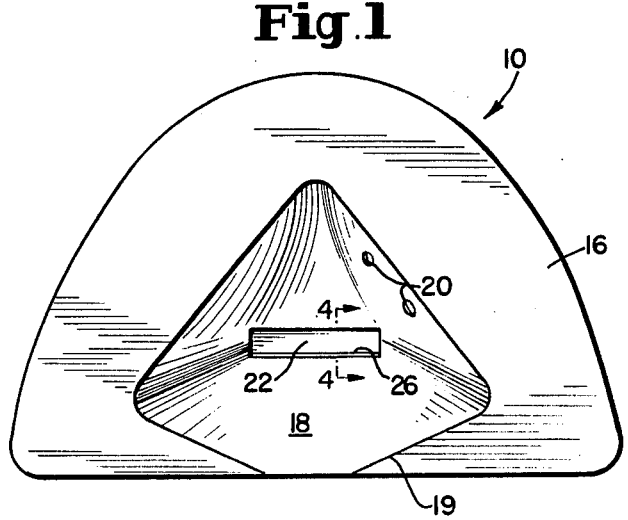
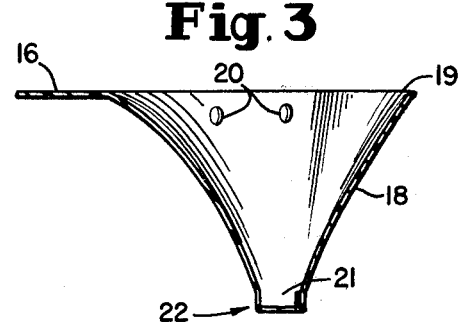
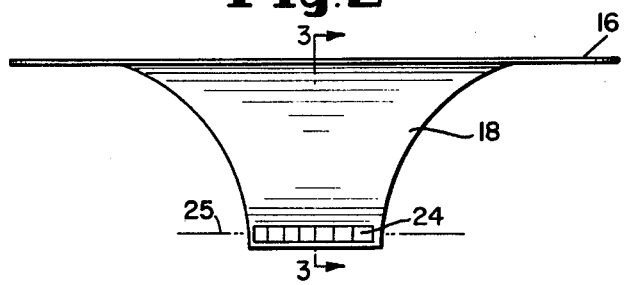
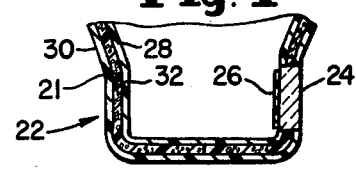
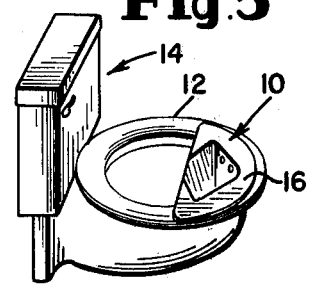
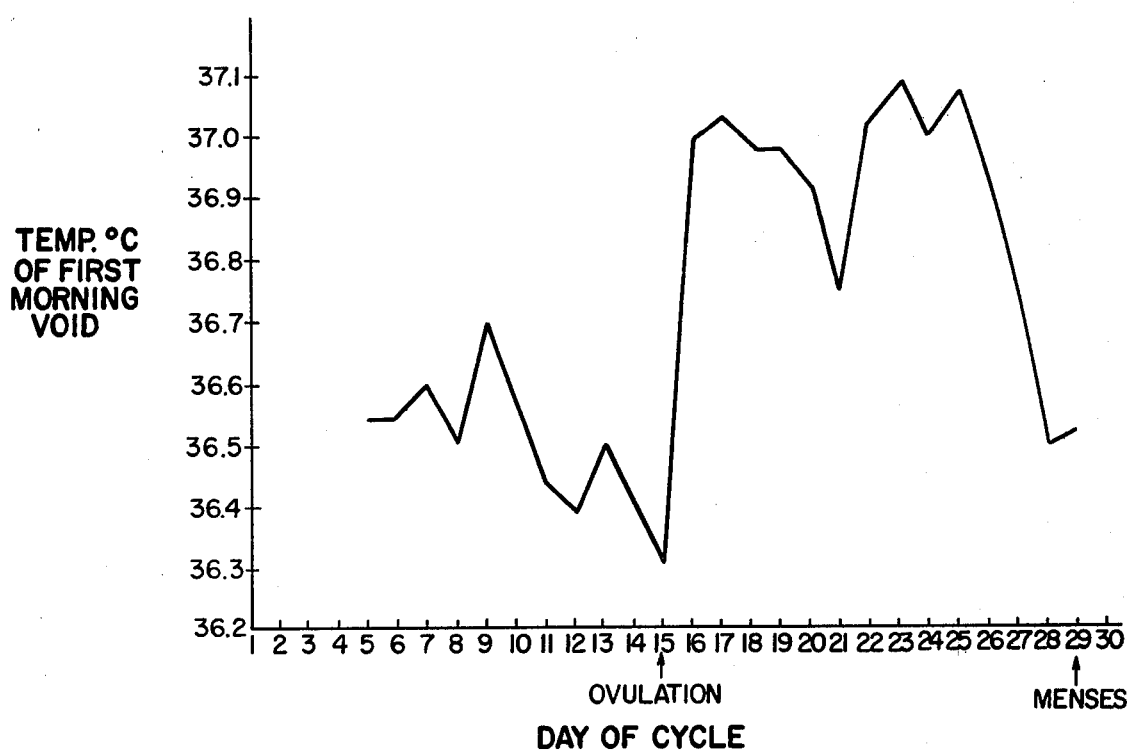
Fig.6
CHANGE IN URINARY TEMPERATURE DURING MENSTRUAL CYCLE

URINARY TEMPERATURE MEASUREMENT DEVICE

This invention relates to a method and apparatus for accurately measuring the core body temperature and, in a preferred embodiment, for measuring the fertility cycle, including the detection of ovulation and pregnancy. The device provides an accurate daily record of the core body temperature which may be plotted on a graph so that ovulation and pregnancy may be rapidly and efficiently detected without clinical tests or the like.

It has been known for many years that a woman's fertility cycle results in changes in core body temperature which coincide with ovulation and pregnancy. An efficient and rapid means to measure core body temperature, however, had not been developed prior to this invention.

For example, the common means for measuring core body temperature in the home consisted of use of an oral thermometer. The oral thermometer, however, does not provide an accurate gauge of core body temperature unless extremely rigorous conditions are pursued. For example, in measuring the fertility or menstrual cycles the temperature should be taken upon awakening in the morning by maintaining the thermometer in the mouth for an extended period of time before arising from bed. Accuracy depends upon maintaining the thermometer for 10 minutes under ideal conditions. This procedure is entirely too confining for most people, and if not repeated regularly on a daily basis will result in inaccurate measurements, and therefore an inaccurate depiction of the fertility cycle.

In the article by Fox et al entitled "Measurement of Deep Body Temperature from the Urine", *Clinical Science and Molecular Medicine* (1975) 48 1-7, the correlation of oral, rectal, and urinary temperatures was measured. Typically, the oral temperature varied widely, and it was concluded that urinary temperature could be used as an accurate measure of core body temperature if the sample could be measured before it was cooled by ambient conditions. Rectal temperature was found to be an accurate measurement, but is not acceptable for general utilization because it is nearly universally recognized as being physically disagreeable.

In an article entitled "Urinary Temperature" by Murray et al appearing in *New England Journal of Medicine*, Vol. 296 No. 1, 23-24 (1977), urinary temperature was recognized as a simple, non-invasive and useful clinical tool in the diagnosis of factitious fever based on simultaneous oral, rectal and urinary temperature measurement.

Accordingly, accurate measurement of body temperature is essential to an accurate depiction of the fertility cycle. While oral and rectal temperature measurements theoretically could accurately depict a temperature change, because the conditions are too rigorous or disagreeable, they can not be depended upon in non-clinical applications.

It has long been recognized that the accurate measurement of changes in body temperature can be recorded to depict the fertility cycle, and the prior art contains various means for attempting to facilitate this measurement.

For example, in U.S. Pat. No. 2,927,463 a means for recording on graph paper the oral temperature is described. In addition, in U.S. Pat. No. 4,151,831, an electronic measurement device is provided with a memory system. In the latter patent, surface or vaginal temperature is automatically recorded in a microprocessor based thermometer and an indication of change provided.

However, as noted above, a simple and efficient means which is also reliable and inexpensive for recording such temperature has not been provided.

As also noted above, in a urinary temperature measurement device an instantaneous temperature reading is desirable to avoid cooling of the specimen due to ambient temperature conditions. The device of this invention utilizes a liquid crystal display to provide such a reading. While liquid crystal thermometers are well known, such displays have not prior to this invention been adapted to measurement of urinary temperatures. For example, in U.S. Pat. No. 3,651,695, a liquid crystal temperature measurement means is provided in a flow conduit for measuring the temperature of a body fluid flowing therethrough. U.S. Pat. No. 2,204,764 also provides a device for measuring fluid temperature. These patents, however, do not describe a simple and efficient means for measuring urinary temperature or for accurately recording changes in core body temperature in a device which may be easily used at home.

In accordance with the basic invention, a urine sampling device attachable to a toilet seat is provided with an insulated chamber therein. Upon arising in the morning the individual using the device voids into the chamber. The insulated chamber mounts a liquid crystal display. The display is then immediately read, the temperature recorded and the device of this invention emptied and washed with tap water. The liquid crystal display provides an instantaneous temperature recording which when used on a regular daily basis will accurately depict changes in body core temperature.

Accordingly, it is an object of this invention to provide a simple and efficient means for measuring core body temperature.

It is another object of this invention to provide a device for measuring urinary temperature which will provide an instanteous readout so that temperature changes related to changes in core body temperatures may be recorded and evaluated.

It is yet another object of this invention to provide a simple and effective means for predicting the fertility cycle by measuring urinary temperature upon arising in the morning so that daily changes in said temperature may be used to accurately depict the fertility cycle.

It is still another object of this invention to provide a relatively inexpensive device which will accurately measure urinary temperature for use in evaluating, clinically, said temperature on a regular or prolonged basis to evaluate changes in body core temperature.

These and other objects will become readily apparent with reference to the drawings and following description wherein:

FIG. 1 is a top view of the device of this invention.

FIG. 2 is a rear view of the device of this invention depicting a typical temperature display.

FIG. 3 is a cross-sectional view taken along lines 3—3 of FIG. 2.

FIG. 4 is a fragmentary cross-sectional view taken along line 4—4 of FIG. 1.

FIG. 5 is a perspective view illustrating the device of this invention mounted on a conventional toilet seat.

FIG. 6 is a typical graph depicting the daily change in urinary temperature as related to body core temperature during the menstrual cycle.

With attention to the drawings and to FIGS. 1 and 5, in particular, this invention includes a urine collection device 10 which may fit on the seat 12 of a conventional toilet 14. In the alternative, a different type of collection device may be utilized within the scope of this invention as will be subsequently described.

In the preferred embodiment, however, the device 10 includes a flange 16 which rests on seat 12 and supports a depending chamber 18 which serves as a funnel to collect freshly voided urine. Funnel 18 includes a mouth 19 and a lower exit port 21.

With attention to FIGS. 2-4, funnel 18 may be equipped with overflow ports 20. Funnel 18 terminates in a collection chamber 22 shown in FIG. 4 in detail.

Chamber 22 mounts an integral window 24, and a liquid crystal temperature measurement array 26 mounted internally thereon. Elongated window 24 has a longitudinal axis 25 extending laterally across chamber 22 as shown in FIG. 2. Chamber 22, or in fact funnel 18 and chamber 22 may be preferably constructed of inner and outer layers 28 and 30 of conventional plastic material. An insulating layer 32 of, for example, styrofoam is sandwiched between layers 28 and 30. Window 24, however, would be an integral piece of clear plastic so that the device 10 will display a temperature reading of the liquid crystal array 26 through window 24.

In use, upon arising in the morning, the device is placed on a toilet seat as shown in FIG. 5 and urine voided thereinto. Following use, the device is lifted and the temperature of the urine therein read through window 24 on the liquid crystal display. The urine is then emptied into the toilet 14 and the device rinsed with tap water.

Liquid crystal temperature units are commercially available. However, a preferred embodiment is available under the trade name "Ovutyme" from Djinnii Industries, Inc., of Dayton, Ohio. The temperature profile for the preferred unit is shown in the table below. The temperatures shown are at the start of the respective color. To use the array, the highest color in a particular vertical row is recorded or a chart may be used for the actual numerical equivalent. For example, with reference to the table below, if the temperature of the urine is 35.5° C., the crystals corresponding to Columns 1, 2 and 3 will record blue. The crystals corresponding to Column 4 will record green and the crystals corresponding to Column 5 will record red, as the temperature responsive color for that particular Column.

| Event | OVUTYME | | | | |
| --- | --- | --- | --- | --- | --- |
|  | 1 | 2 | 3 | 4 | 5 |
| Visible Start | 34.0 | 34.35 | 34.6 | 35.0 | 35.2 |
| Start at Red | 34.15 | 34.7 | 34.9 | 35.25 | 35.5 |
| Start at Green | 34.8 | 34.9 | 35.25 | 35.3 | 35.9 |
| Start at Blue | 34.9 | 35.35 | 35.5 | 35.9 | 36.2 |

As will be obvious to those skilled in the art, other types of liquid crystal arrays may be provided. However, the critical feature is an instantaneous temperature reading which is easily recorded either as a code or an actual temperature reading.

With reference to FIG. 6, FIG. 6 depicts a typical chart of urinary temperature fluctuations during a menstrual cycle. As shown therein at day 15, a sharp temperature drop followed by a sharp temperature increase indicates ovulation. Beginning at day 25, the temperature drop indicates the onset of menses. Had ovulation been followed by pregnancy the drop in temperature beginning at day 25 would not have occured.

In summary then, the device of this invention comprises an insulated receptacle with a temperature responsive liquid crystal array therein. The liquid crystals accurately and instantaneously record the temperature of the urine collected therein, and this temperature may then be readily recorded upon viewing through a transparent window in the device.

The device is particularly useful in providing an accurate and easily determined measurement of the body core temperature. Changes in body core temperature, as is known, are important in studying many disease conditions. In addition, an accurate recording of body core temperature is particularly useful in recording or depicting the fertility cycle or menstrual cycle in women.

In recording the menstrual cycle, the device of this invention is utilized to collect the first morning void of urine. In this case, the temperature may be recorded each morning as a regular event on a graph thereof. Changes in the temperature then will provide an accurate and dependable means for determining ovulation or pregnancy without clinical tests or complicated equipment.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for measuring core body temperature in humans comprising: a funnel shaped receptacle having a mouth and an exit port adapted to receive urine voided directly thereinto; a chamber integrally attached to said receptacle at the exit port thereof for receiving at least a portion of the urine voided thereinto; said chamber having a base and upstanding walls and a transparent window mounted in at least a portion of said upstanding walls; liquid crystal temperature measurement means mounted within said chamber and affixed to said window for registering the temperature of urine voided into said receptacle and said chamber and for displaying said temperature registration through said window for external view.

2. The device of claim 1, further comprising means carried by said receptacle for mounting said device on a toilet seat.

3. The device of claim 2, wherein the walls and base of said chamber are constructed of heat insulating material.

4. The device of claim 3, wherein said liquid crystal means has a range of temperature registration of from about 35° to about 37° C., and a display accurate to about 0.2° C. within said range.

5. The device of claim 1, wherein the walls of said chamber extend integrally from the periphery of the exit port of said receptacle and the window has a longitudinal axis contained in a plane parallel to a plane containing the base.

6. The device of claim 2, wherein said mounting means further comprises a flange carried by said receptacle and extending outwardly from the mouth thereof, a portion of said flange adapted to rest on a toilet seat.

7. The device of claim 1, wherein said receptacle further comprises overflow port means disposed adjacent the mouth thereof so that said device will not overflow when urine is voided thereinto.

* * * * *